United States Patent [19]

Sammarco

[11] Patent Number: 5,766,259
[45] Date of Patent: Jun. 16, 1998

[54] TOTAL ANKLE PROSTHESIS AND METHOD

[76] Inventor: Giacomo J. Sammarco, 430 W. Cliff La., Cincinnati, Ohio 45220

[21] Appl. No.: 777,568

[22] Filed: Dec. 31, 1996

Related U.S. Application Data

[63] Continuation of Ser. No. 403,647, Mar. 14, 1995, abandoned.

[51] Int. Cl.$^6$ ............................................. A61F 2/42
[52] U.S. Cl. ............................................. 623/21
[58] Field of Search ...................... 623/21; 606/87, 606/86, 96

[56] References Cited

U.S. PATENT DOCUMENTS

| | | | |
|---|---|---|---|
| 3,872,519 | 3/1975 | Giannestras et al. | |
| 3,987,500 | 10/1976 | Schlein | 623/21 |
| 4,156,944 | 6/1979 | Schreiber et al. | 623/21 |
| 4,232,404 | 11/1980 | Samuelson et al. | 623/21 |
| 4,340,978 | 7/1982 | Buechel et al. | 623/20 |
| 4,470,158 | 9/1984 | Pappas et al. | 623/20 |
| 4,755,185 | 7/1988 | Tarr | 623/18 |
| 5,122,144 | 6/1992 | Bert et al. | 606/88 |
| 5,326,365 | 7/1994 | Alvine | 623/21 |

FOREIGN PATENT DOCUMENTS

| | | | |
|---|---|---|---|
| 2220235 | 10/1974 | France | 623/21 |
| 2684291 | 6/1993 | France | 623/21 |

OTHER PUBLICATIONS

*Total Ankle Replacement*, F.F. Buechel, and J.D. Heckman, Expert Exchange, vol. 1, No. 2, pp. 123–130 (1990).
*Survivorship and Clinical Evaluation of Cementless, Meniscal–Bearing Total Ankle Replacements*, F.F. Buechel and M.J. Pappas, Seminars in Arthroplasty, vol. 3, No. 1, pp. 43–50 (Jan. 1992).
Drawing page—*Implant Usage*, Buechel–Pappas™Custon Total Ankle System, ENDOTEC.

R.N. Stauffer, *Total Ankle Joint Replacement*, Symposium on Total Joint Replacement, vol. 112, pp. 1105–1109 (Sep. 1977).
*Salvage Procedures for Complications of Total Ankle Arthroplasty*, H.E. Groth and H.F. Fitch, Clinical Orthopaedics and Related Research, No. 224, pp. 244–250 (Nov. 1987).
*Comparative Analysis of Ankle Arthroplasty Versus Ankle Arthrodesis*, M.R. McGuire et al., Clinical Orthopaedics and Related Research, No. 226, pp. 174–181 (Jan. 1988).
*Force and Motion Analysis of the Normal, Diseased, and Prosthetic Ankle Joint*, R.N. Stauffer, et al., Clinical Orthopaedics and Related Research, No. 127, pp. 189–196 (Sep. 1977).
*An Artifical Ankle Joint*, St. E.N. Newton, Clinical Orthopaedics and Related Research, No. 142, pp. 141–145 (Jul.–Aug. 1979).

(List continued on next page.)

*Primary Examiner*—David H. Willse
*Attorney, Agent, or Firm*—Frost & Jacobs LLP

[57] ABSTRACT

Prosthesis components and a method for replacing the articulating surfaces of an ankle joint. Through the use of appropriate guide tools for a surgical saw, planar surfaces are formed on the tibia, talus and fibula. Tibial, talar and fibular prosthesis components are provided for mounting on the tibial, talar and fibular planar cut surfaces, respectively. A floating bearing is located between the tibial and talar prosthesis components. The floating bearing makes full contact with the talar prosthesis component and is capable of limited medial-lateral and fore and aft movement with respect to the tibial prosthesis component. The fibular prosthesis component has a plastic insert which cooperates with the other prosthesis components to provide stability to the ankle joint by permitting the full range of motion of the fibula including sliding motion fore and aft, piston-like motion up and down, and rotation.

20 Claims, 12 Drawing Sheets

OTHER PUBLICATIONS

*Evaluation of the Early Result of Smith Total Ankle Replacement*, A.A. Dini and F.H. Bassett, Clinical Orthopaedics and Related Research, No. 146, pp. 228–230 (Jan.–Feb. 1980).

*Salvage of Painful Total Ankle Arthroplasty*, R.N. Stauffer, Clinical Orthopaedics and Related Research, No. 170, pp. 184–188 (Oct. 1982).

*Total Ankle Replacement A New Approach to an Old Problem*, G.A. Zych and W.Mnaymned, J. Florida, vol. 66, No. 1, pp. 96–100 (Jan. 1979).

*Can The Ankle Joint Be Replaced?* D.L. Hamblen, The Journal of Bone and Joint Surgery, vol. 67–B, No. 5, pp. 689–690 (Nov. 1985).

*Total Ankle Arthroplasty, A Long–Term Review of the London Hospital Experience*, B.G. Bolton–Maggs, et al., The Journal Of Bone And Joint Surgery, vol. 67–B, No. 5, pp. 785–790 (Nov. 1985).

*Total Ankle Replacement In Rheumatoid Arthritis*, P.F. Lachiewicz, et al., The Journal Of Bone And Joint Surgery, vol. 66–A, No. 3, pp. 340–343 (Mar. 1984).

*Total Ankle Arthroplasty*, St. Elmo Newton, The Journal Of Bone and Joint Surgery, vol. 64–A, No. 1, pp. 104–111 (Jan. 1982).

*Clinical Study of Total Ankle Replacement with Gait Analysis*, J.D. Demottaz, et al., The Journal Of Bone And Joint Surgery, vol. 61–A, No. 7 pp. 976–988 (Oct. 1979).

*Total Joint Arthroplasty, The Ankle*, R.N. Stauffer, Mayo Clin Proc., vol. 54, pp. 570–575 (Sep. 1979).

*Irvine Ankle Arthroplasty*, T.R. Waugh, et al., Clinical Orthopaedics and Related Research, No. 114, pp. 180–184 (Jan.–Feb. 1976).

*MR Imaging of the Tarsal Tunnel and Related Spaces: Normal and Abnormal Findings with Anatomic Correlation*, S.J. Erickson, et al., AJR, vol. 155, pp. 323–328 (Aug. 1990).

*Salvage of Nonunion Following Ankle Arthrodesis for Failed Total Ankle Arthroplasty*, H.B. Kitaoka, Clinical Orthopaedics and Related Research, No. 268, pp. 37–43 (Jul. 1991).

*Ankle Arthroplasty*, Y. Takakura et al., Clinical Orthopaedics and Related Research, No. 252, pp. 209–216 (Mar. 1990).

TOTAL ANKLE PROSTHESIS AND METHOD

This is a continuation, of application Ser No. 08/403,647, filed Mar. 14, 1995, now abandoned.

TECHNICAL FIELD

The present invention relates to a total ankle prosthesis and method, and more particularly to such a prosthesis and method involving the use of a tibial prosthesis component and a talar prosthesis component with a floating bearing therebetween, as well as a fibular prosthesis component.

BACKGROUND ART

For many years there has been considerable interest and activity with respect to a total ankle prosthesis as a viable approach to the treatment of diseased or injured ankle joints.

Fusion has long been an alternative to total ankle arthroplasty. This approach has its drawbacks. For example, there is a loss of motion in the ankle joint which may cause difficulties with other associated parts of the leg, such as the knee joint.

Many types of total ankle prostheses have been developed including the cylindric-type ankle replacement, the spherical-type ankle replacement, the sliding cylindric-type ankle replacement, to name a few. U.S. Pat. No. 3,872,519 is illustrative of an early approach to total ankle prosthesis. The most usual prior art total ankle prosthesis comprises a tibial prosthesis component and a talar prosthesis component which work directly with each other. No prosthesis component has been provided for the fibula. Some of the most common problems encountered with prior art total ankle prostheses are loosening of the components, instability, and inadequate motion.

The present invention is based upon the discovery that these and other prior art problems can be markedly reduced or eliminated by the provision of a total ankle prosthesis comprising a tibial prosthesis component, a talar prosthesis component, a floating bearing between the tibial and talar prosthesis components, together with a fibular prosthesis component enabling the fibula to perform its usual unique functions.

The floating bearing has total contact with the talar prosthesis component. The floating bearing has a controlled freedom of motion with respect to the tibial prosthesis component, allowing fore and aft motion therebetween, as well as side-to-side movement which reduces bone/prosthesis component interface stress. Furthermore, the fibula retains and is capable of all of its usual micro-motions including pistoning, rotation, and outward bending. Articulation between the fibular prosthesis component and the talar prosthesis component is present. As a result of these features, the fibula can perform its usual purpose, that of acting as a stabilizer for the ankle joint, both side-to-side and fore and aft.

DISCLOSURE OF THE INVENTION

According to the invention there is provided a method and prostheses for replacing the articulating surfaces of an ankle joint. By means of a surgical saw with an oscillating blade and appropriate blade guide tools positioned by the ankle joint, itself, planar surfaces are formed on the tibia, talus and fibula. Tibial, talar and fibular prosthesis components are mounted on the tibial, talar and fibular planar support surfaces, respectively. The tibial and talar prosthesis comprise metallic members, each of which may be provided with integral mounting and locating pins adapted to be received in appropriately positioned bores in the tibia and talus, respectively. The tibial and talar prosthesis components may be adhered to their respective support surfaces by cement, or by bio-ingrowth. The fibular prosthesis component is affixed to the fibula support surface by cement. The fibular prosthesis component carries a plastic insert capable of contacting and cooperating with the other prosthesis components.

A plastic floating bearing is provided and is located between the tibial prosthesis component and the talar prosthesis component. The tibial prosthesis component has a depression formed therein having a planar bottom. The floating bearing has an upper extension terminating in a planar surface. The extension of the floating bearing is receivable in the depression of the tibial prosthesis component with their respective planar surfaces in abutting relationship. The floating bearing extension and the tibial prosthesis component depression are so dimensioned as to permit controlled fore and aft movement and side-to-side movement of the floating bearing with respect to the tibial prosthesis component. The floating bearing makes full contact with the talar prosthesis component. The prosthesis components and floating bearing simulate the original articulating surfaces of the ankle joint to enable proper movement of the parts thereof.

DETAILED DESCRIPTION OF THE INVENTION

Throughout the Figures like parts have been given like index numerals. The tools and prosthesis components of the present invention, together with their method of use, will be described with respect to a total ankle prosthesis involving a left foot. It will be understood by one skilled in the art that the prosthesis tools and prosthesis components used in association with a right foot will be mirror images of the tools and prosthesis components described, while the method will be substantially identical.

Figure 1:
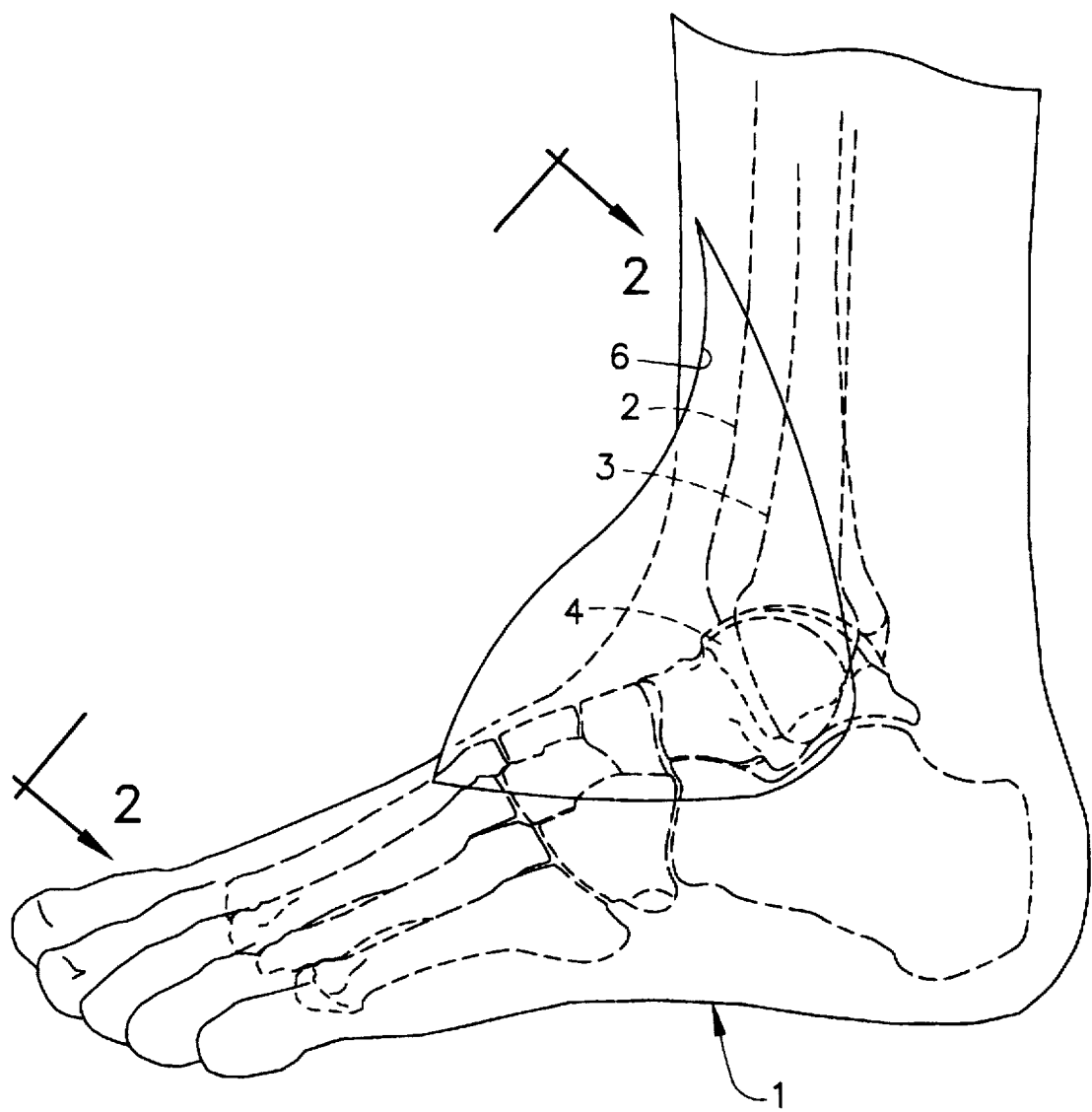
FIG. 1 is a fragmentary lateral elevational view of a left human foot in neutral position, with some of the bone structure indicated in broken lines and with an incision diagrammatically illustrated.
Figure 2:
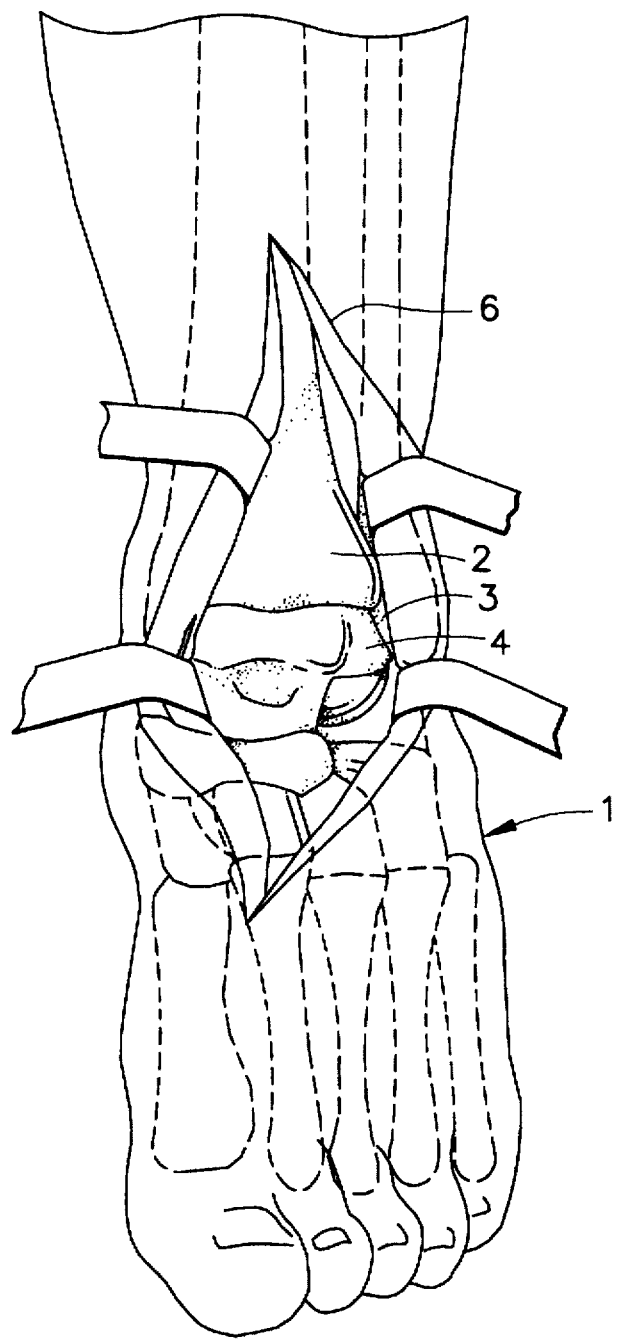
FIG. 2 is a fragmentary front elevational view of the foot of FIG. 1 as seen from the left of FIG. 1.
Figure 3:
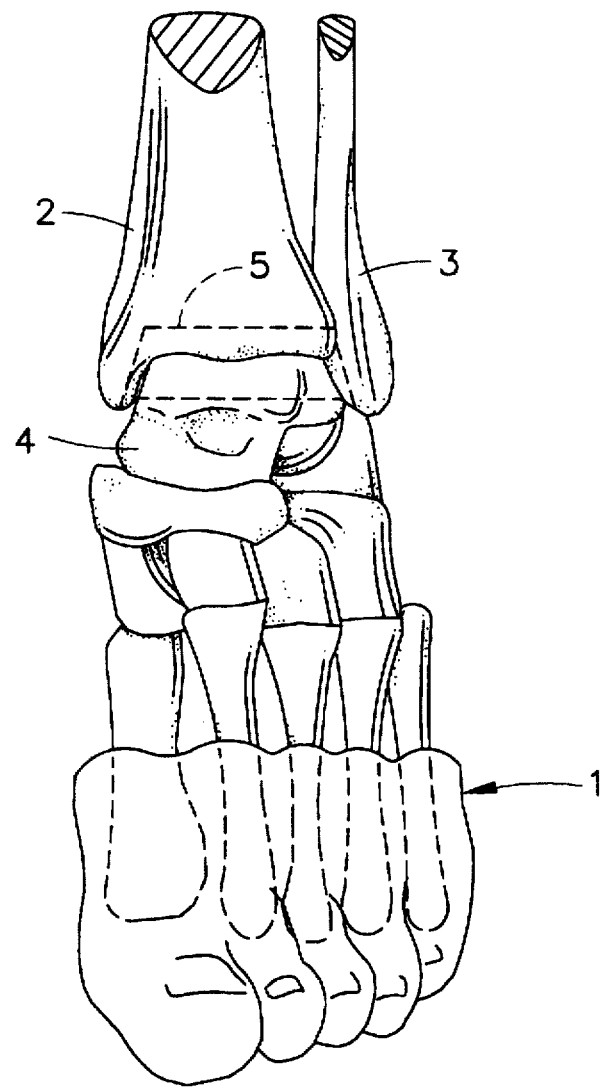
FIG. 3 is a fragmentary front elevational view, similar to FIG. 2, and more clearly illustrating the bone structure and the area to be occupied by the total ankle prosthesis.

Reference is first made to FIGS. 1, 2 and 3 wherein a left foot is illustrated at 1. FIGS. 1, 2 and 3 also illustrate most of the foot bones and the lower ends of the lower leg bones. The procedure of the present invention involves three of these bones: the tibia 2, the fibula 3 and the talus 4.

The area of concern with respect to the present invention involves all three of these bones, and is outlined by the broken-line trapezoid 5 of FIG. 3. To access the area indicated at 5, an incision 6 is made. The incision 6 is somewhat diagrammatically indicated in FIG. 1 and is shown more clearly in FIG. 2. The length of incision 6 will depend, among other things, on the size of the patient. In most instances, an incision of about 10 cm in length will suffice.

Figure 4:
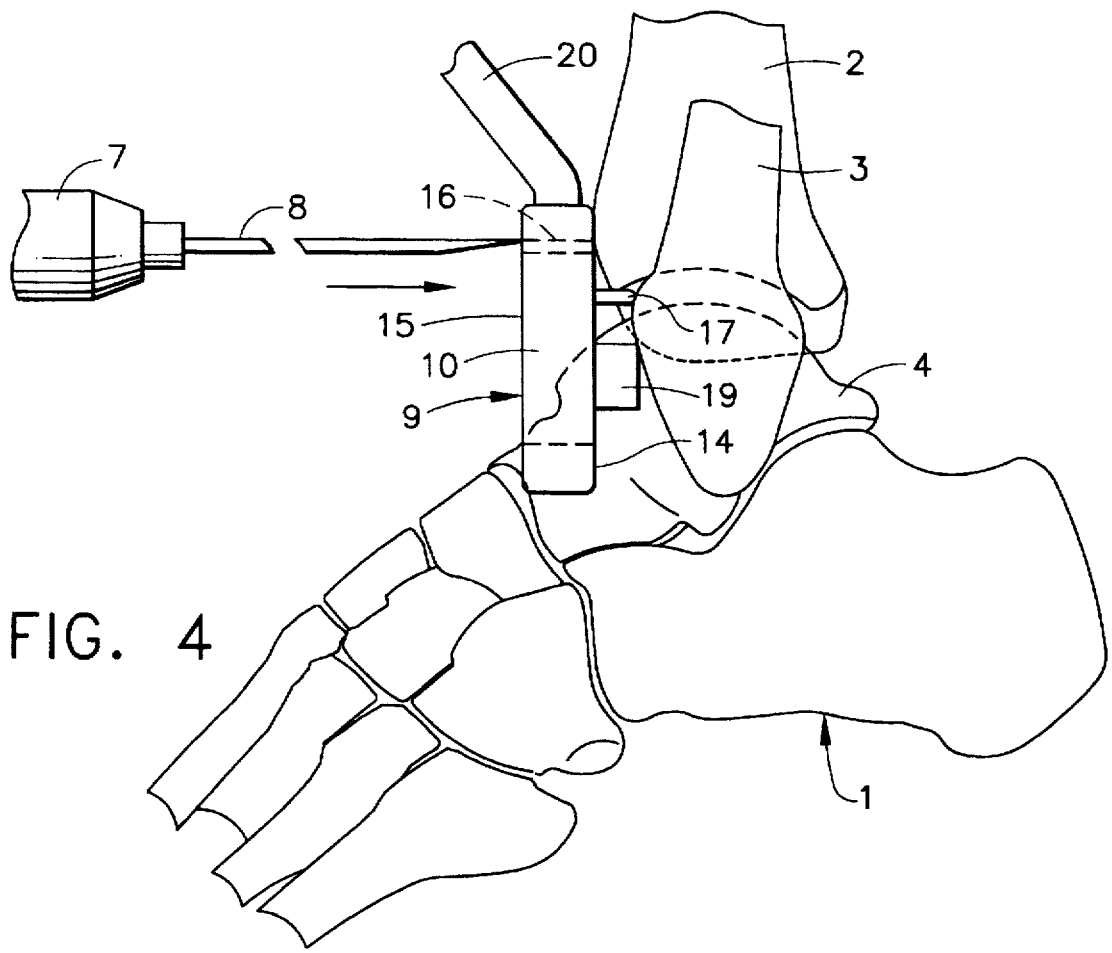
FIG. 4 is a fragmentary lateral elevational view of the bone structure of FIG. 3 illustrating a tibia/fibula saw guide, and its placement for use with an oscillating surgical saw.
Figure 5:
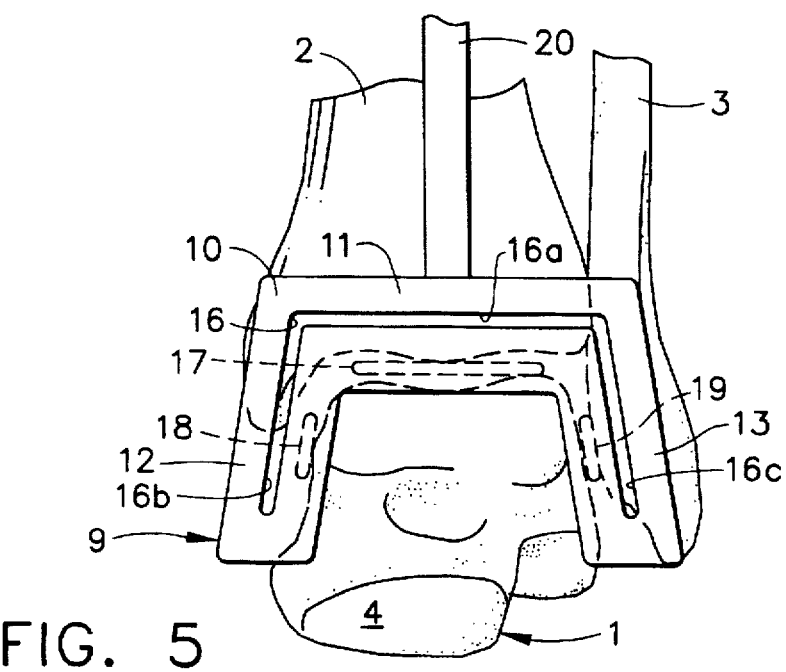
FIG. 5 is a fragmentary front elevational view of the bone structure and saw guide of FIG. 4, as seen from the left in FIG. 4.
Figure 6:
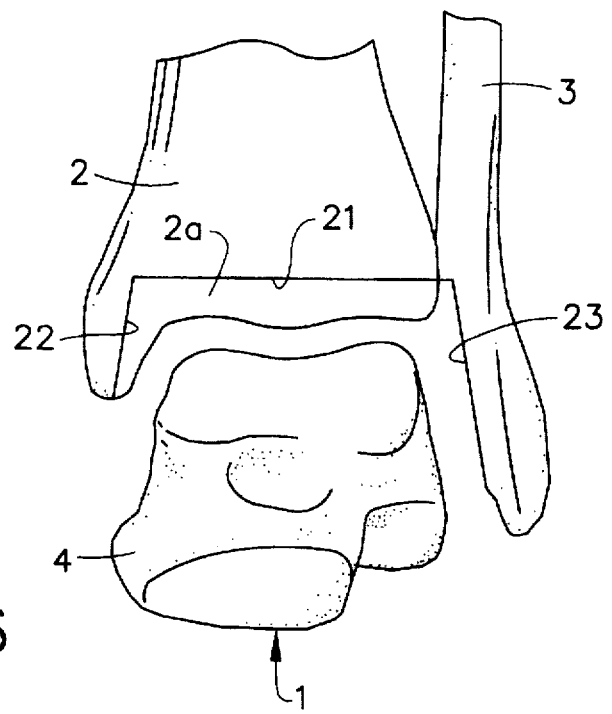
FIG. 6 is a fragmentary front elevational view, similar to FIG. 5, with the tibia/fibula saw guide removed to show the cuts made in the tibia and fibula.

When the incision 6 has been made, and the area 5 of interest has been exposed (as shown in FIG. 2), the next series of steps is to form the desired cut surfaces on the tibia 2 and the fibula 3. Reference is made to FIGS. 4, 5 and 6. Turning first to FIGS. 4 and 5, the cut surfaces are formed on the tibia 2 and fibula 3 by a conventional oscillating surgical saw 7 which actuates a thin blade 8. The cuts are made with the aid of a tool in the form of a tibia/fibula cutting guide, generally indicated at 9. As is best shown in FIGS. 4 and 5, the tibia/fibula cutting guide 9 comprises a substantially inverted U-shaped guide body 10 having a horizontal base portion 11 and downwardly and outwardly directed leg portions 12 and 13 (as viewed in FIG. 5). It will be understood by one skilled in the art that, as used herein and in the claims, phrases such as "horizontal", "vertical", "upwardly", and "downwardly", "upper", "lower", etc., are used strictly for clarity of description and in conjunction with the drawings. The patient's foot, as well as the tools taught herein, may assume one or more of a variety of positions during the procedure.

The body 10 of tibia/fibula cutting guide 9 has a planar forward surface 14 and a planar rearward surface 15. Guide body 10 has a slot 16 extending from its rearward surface 15 through its forward surface 14. The slot 16 is of substantially inverted U-shaped configuration comprising a rectilinear base portion 16a, a first downwardly and outwardly extending leg portion 16b and a second downwardly and outwardly extending leg portion 16c.

The tibia/fibula cutting guide body 10 has three locating fins 17, 18 and 19 projecting forwardly from its forward surface 14. The fins 17, 18 and 19 are substantially parallel to the guide slot portions 16a, 16b and 16c, respectively. As is shown in FIGS. 4 and 5, with the patient's foot in a neutral or slightly plantarflexed position, the fins 17, 18 and 19 are adapted to be inserted into the ankle joint with locating fin 17 adjacent the top of the talus 4 and the medial and lateral locating fins 18 and 19 adjacent the medial and lateral sides of talus 4. In this way, the tibia/fibula cutting guide 9 is properly located by the ankle joint, itself, and the ankle joint, in turn, is properly centered by the cutting guide 9. The cutting guide 9 is manually held in place during the cutting operation by means of a handle, fragmentarily shown at 20. The handle 20 may have any appropriate configuration designed for ease of use and should be sufficiently sturdy to properly hold the cutting guide 9 in place during the cutting operation. Once the cutting guide 9 is in place, the sawblade 8 of the oscillating surgical saw 7 is guided by the guide slot segments 16a, 16b and 16c to form tibial cuts 21 and 22, and fibular cut 23, respectively, as shown in FIG. 6. The tibial cuts 21 and 22 leave a small rear wall on the tibia, as at 2a.

The cutting guide body 10 may be made of any appropriate material, such as stainless steel, or the like, which is suitable for use in a surgical environment and is capable of being sterilized. The guide body 10 could, for example, be fabricated of sheet metal.

Figure 7:
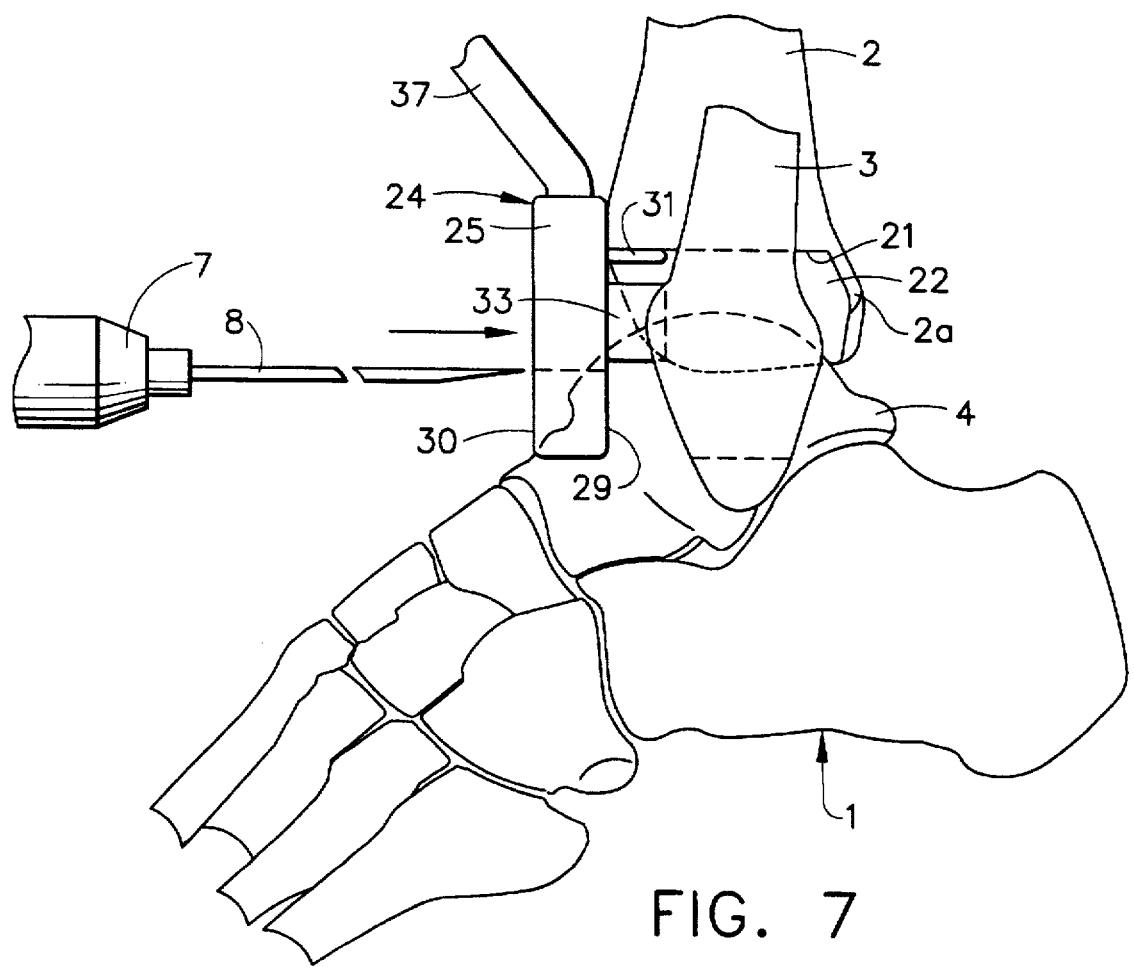
FIG. 7 is a fragmentary lateral elevational view similar to FIG. 4 and illustrating the talus saw guide and its positioning for use with an oscillating surgical saw.
Figure 8:
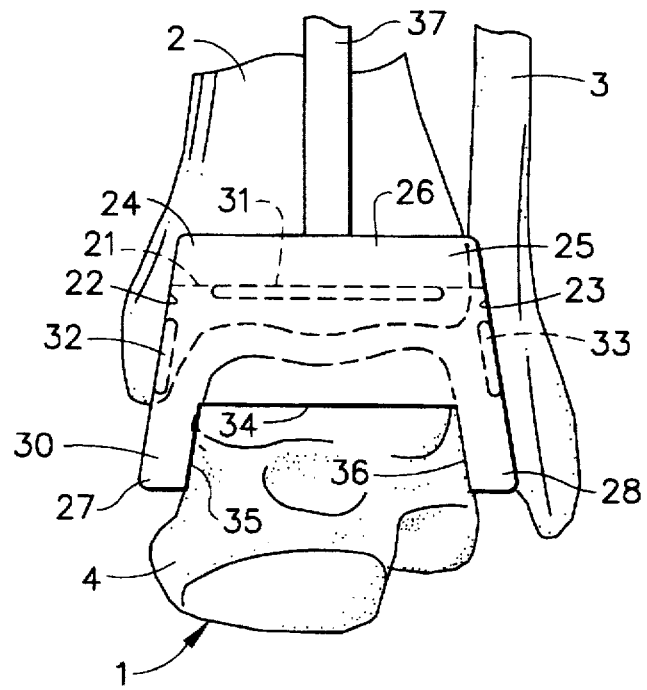
FIG. 8 is a fragmentary front elevational view, as seen from the left of FIG. 7, illustrating the talus saw guide in position.

The cuts 21 and 22 having been made in the tibia 2 for its prosthesis component, and the cut 23 having been made in the fibula 3 for its prosthesis component, the next step is to make appropriate cuts in the talus 4 to prepare it for receipt of its prosthesis component. To this end, a tool in the form of a talus cutting guide, generally indicated at 24, is provided for use with the oscillating surgical saw 7 and its blade 8. The talus cutting guide 24 is best shown in FIGS. 7 and 8. The talus cutting guide comprises a body 25 and, as viewed in FIG. 8, has a horizontal base portion 26 and a pair of downwardly and outwardly extending legs 27 and 28. The talus cutting guide body 25 has a planar forward surface 29 and a planar rearward surface 30. The body 25 may be made of any appropriate, surgically compatible, sterilizable material such as stainless steel or the like. The talus cutting guide body could also be fabricated of sheet metal, or even an appropriate plastic material compatible with a surgical environment and sterilizable. As in the case of the tibia/fibula cutting guide 9, the forward face 29 of talus cutting guide body 25 has 3 forwardly extending locating fins 31, 32 and 33. As viewed in FIGS. 7 and 8, the fin 31 extends from the base portion 26 of the talus cutting guide body 25 and is spaced downwardly from the upper surface of the talus cutting guide body 25. The fin 32 comprises a medial fin, the outside surface thereof being substantially coplanar with the medial outside surface of talus cutting guide leg portion 27. In a similar fashion, the fin 33 comprises a lateral fin, the outside surface of which is substantially coplanar with the lateral surface of the talus cutting guide leg 28. Instead of a cutting guide slot such as portions 16a, 16b and 16c of slot 16 of the tibia/fibula cutting guide 9, the talus cutting guide 24 is provided with exterior cutting guide surfaces 34, 35 and 36, as is best shown in FIG. 8. The talus cutting guide 24 has a handle 37 which, as in the case of handle 20 of FIGS. 4 and 5, should be such as to enable the surgeon to maintain the talus cutting guide in place, during the cutting operations performed upon the talus.

Figure 9:
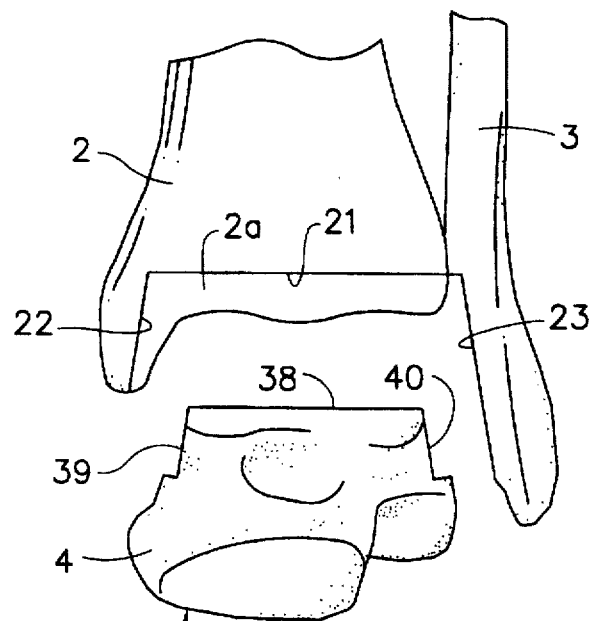
FIG. 9 is a fragmentary front elevational view, illustrating the cuts made on the talus by means of the talus saw guide.

To prepare the talus for its prosthesis component the fins 31, 32 and 33 of the talus cutting guide 24 are inserted in the ankle joint as shown in FIGS. 7 and 8 with the patient's foot in a neutral or slightly plantarflexed position. In this instance, the talus cutting guide 24 is properly located by virtue of the engagement of its fins 31, 32 and 33 on the tibial cut surfaces 21 and 22 and the fibular cut surface 23, respectively. The oscillating surgical saw 7 and its blade 8 are used to make cuts along the talus cutting guide surfaces 34, 35 and 36, creating cut surfaces 38, 39 and 40, respectively on the talus 4, as is illustrated in FIG. 9. Using the cut surfaces 21 and 22 of the tibia and cut surface 23 of the fibula as reference surfaces for the placement of the talus cutting guide 24 assures the proper distance between cut surfaces 21, 22 and 23 of the tibia and fibula and the corresponding cut surfaces 38, 39 and 40 of the talus.

Figure 10:
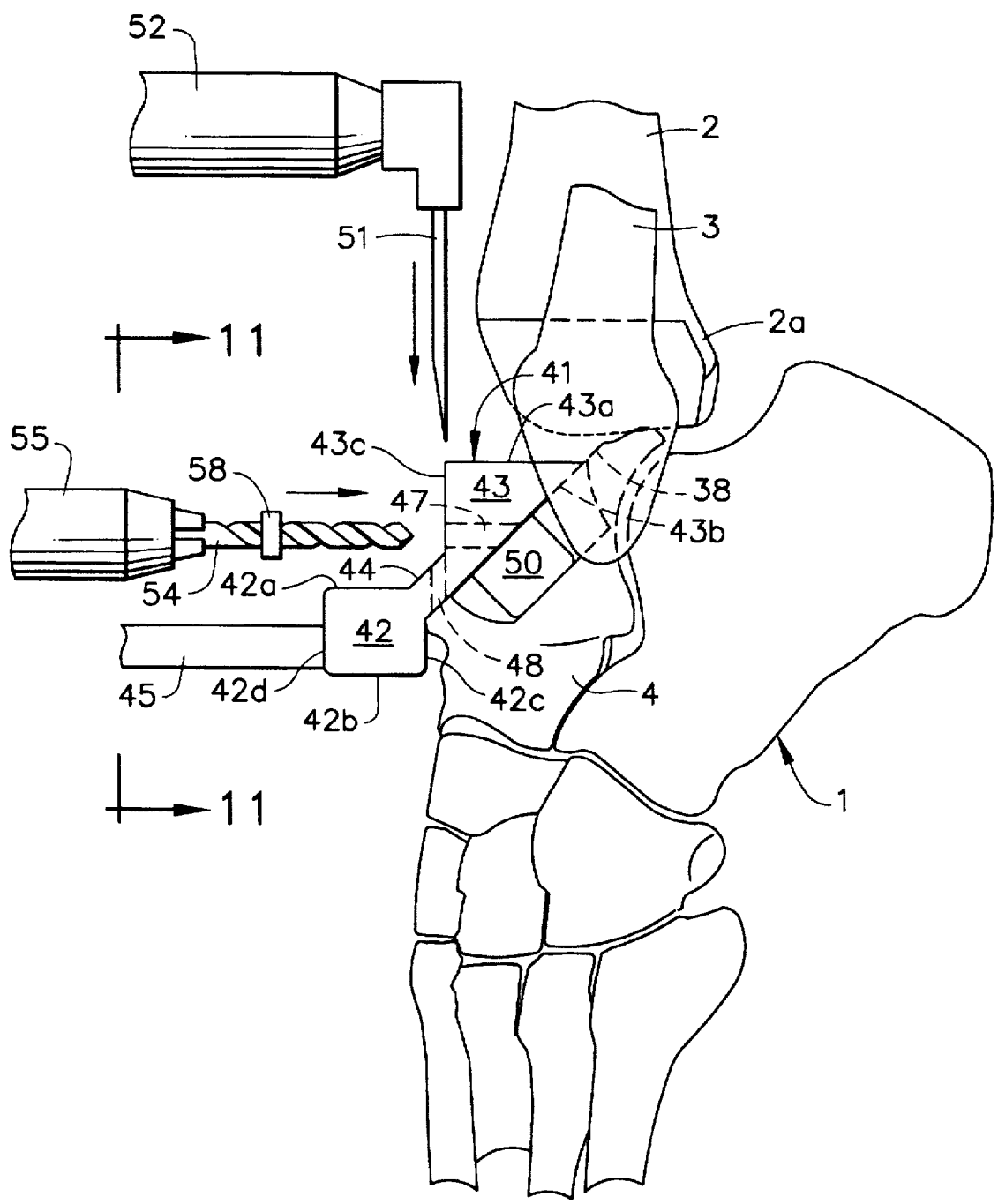
FIG. 10 is a fragmentary lateral elevation of the bone structure of FIG. 3 in plantarflexed position, illustrating the drill and chamfer guide for making an anterior chamfer cut on the talus with an oscillating surgical saw and for drilling a pair of bores in the talus, utilizing a surgical drill.
Figure 11:
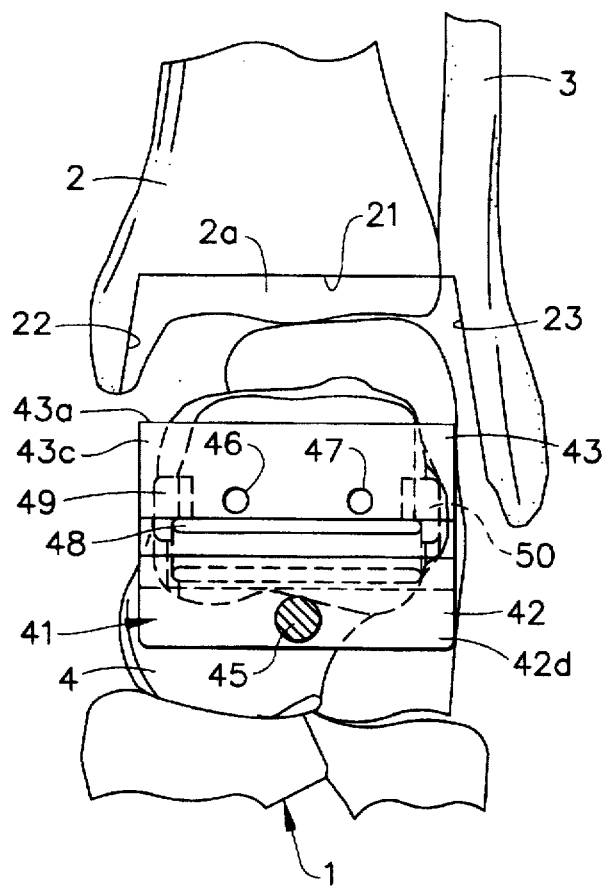
FIG. 11 is a fragmentary front elevational view of the bone structure and drill and chamfer guide of FIG. 10, as seen from the left of FIG. 10.
Figure 12:
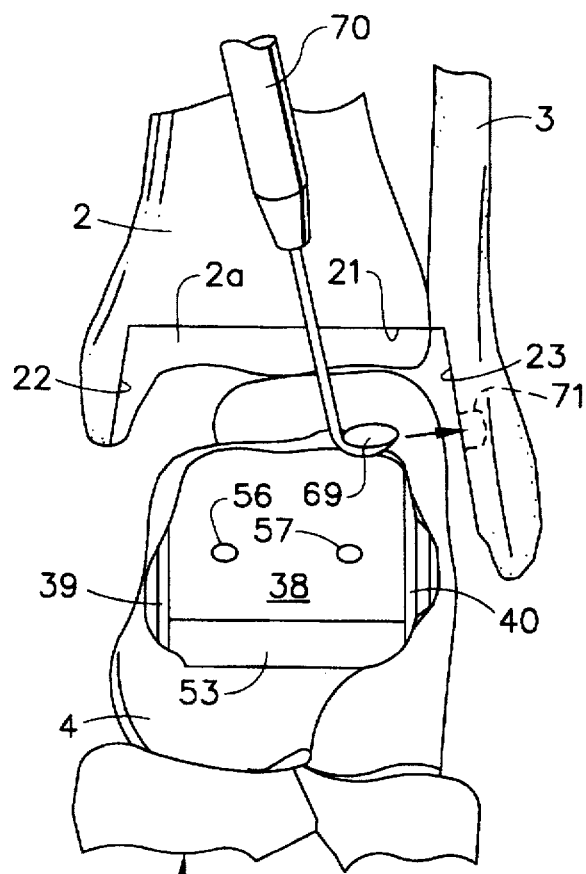
FIG. 12 is a fragmentary front elevational view similar to FIG. 11 with the chamfer guide removed to show the chamfer cut and the pair of bores formed in the talus, and further illustrating means for preparing the cut surface of the fibula.

To complete the talus for receipt of its prosthesis component, it is necessary to make one more anterior talar chamfer cut and to provide the cut surface 38 of the talus with a pair of locating and mounting bores. Reference is made to FIGS. 10, 11 and 12. As shown most clearly in FIG. 10, the foot 1 is placed in a plantarflexed position. To provide the bores in the surface 38 of talus 4 and to provide the anterior chamfer cut thereon, a tool, generally indicated at 41, comprising a talus chamfer cut and drill guide is used. The chamfer cut and drill guide 41 has a body comprising first and second block-like portions 42 and 43 interconnected by a short intermediate neck portion 44. The body may be made of any appropriate material suitable for use in a surgical environment and capable of sterilization, such as stainless steel or the like. As viewed in FIGS. 10 and 11, block-like body portion 42 has a horizontal top surface 42a, a horizontal bottom surface 42b, and vertical forward and rearward surfaces 42c and 42d respectively. A handle 45 is affixed to the block-like portion 42 at its rearward surface 42d. The handle 45 is used to hold the chamfer cut and drill guide 41 in place during the cutting and drilling operations. At the juncture of surfaces 42a and 42c the neck 44 extends upwardly and forwardly forming an angle of 135° with both surfaces 42a and 42c.

The second block-like portion 43 of the chamfer cut and drill guide 41 has planar upper and lower surfaces 43a and 43b. It will be noted that the bottom surface of neck portion 44 and the bottom surface 43b of block-like portion 43 are coplanar. The rearward surface 43c extends downwardly to neck portion 44. At the juncture of neck 44 and surface 43c, a pair of drill bit guide bores 46 and 47 (see also FIG. 11) are formed in the block portion 43 of the chamfer cut and drill guide 41. The axes of the bores 46 and 47 are perpendicular to the surface 43c. At the juncture of the surface 43c and the neck 44 there is a slot 48 which extends through the neck portion 44. The forward surface of the slot, as viewed in FIG. 10, constitutes a continuation of the surface 43c. The chamfer cut and drill guide 41 is completed by a pair of medial and lateral fins 49 and 50 (see FIG. 11). The fins extend from the surface 43b of the block-like portion 43 of the drill and chamfer cut guide 41. The fins 49 and 50, as shown in FIG. 11, are slightly divergent so that they can engage the medial and lateral cut surfaces 39 and 40 of talus 4 (see FIG. 9).

With the foot 1 in plantarflexed position, as shown in FIG. 10, the chamfer cut and drill guide 41 is located on the talus 4 as shown in FIGS. 10 and 11. The bottom surface 43b of the chamfer cut and drill guide 41, together with the coplanar surface of the neck portion 44 are located upon the cut surface 38 of talus 4 with the forward surface 42c of the block-like portion 42 abutting the adjacent surface of the talus 4. The chamfer cut and drill guide 41 is centered from a medial and lateral standpoint by the engagement of the fins 49 and 50 on the talar cut surfaces 39 and 40.

Figure 13:
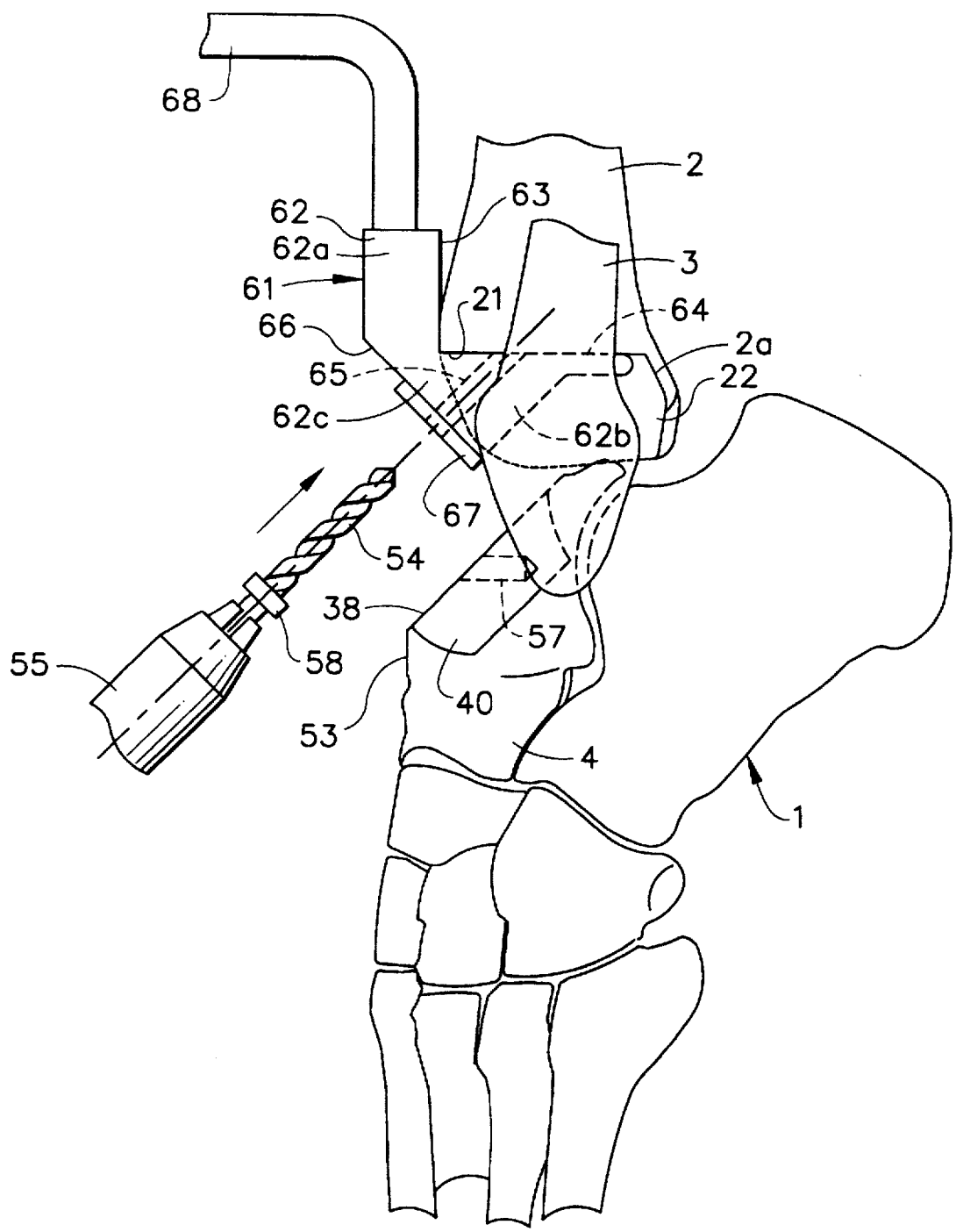
FIG. 13 is a fragmentary lateral elevation of the bone structure in plantar flexed position, and illustrates the positioning and use of a tibia drill guide to provide a pair of bores in the upper cut surface of the tibia.

Once the chamfer cut and drill guide 41 is properly located on the talus 4, the blade 51 of a conventional oscillating surgical saw 52 is inserted through slot 48 to produce the chamfer cut surface 53 (see FIGS. 12 and 13). The chamfer cut surface lies at an angle of about 135° to the cut surface 38.

The surface 42c of the chamfer cut and drill guide 41 is abutted against the just formed chamfer cut surface 53, and the bit 54 of a conventional surgical drill 55 is inserted in each of the drill guide bores 46 and 47 of the chamfer cut and drill guide 41 to form bores 56 and 57 in the cut surface 38 of talus 4. The axes of bores 56 and 57 form an angle of 45° with cut surface 38, as is evident from FIG. 13. To assure proper depth of bores 56 and 57, the surgical drill bit 54 may be provided with a depth or gauge determining collar 58. At this point, preparation of the talus 4 is complete, as shown in FIG. 12. Furthermore, the anterior chamfer cut 53 is the last saw cut required by the procedure.

As is well known in the art, and depending upon the size of the patient, some of the cuts heretofore described cannot be completed while the saw blade guide tool is in place. This is true because the length of the saw blade may be insufficient to complete the cut. However, in such an instance, the depth of the cut made with the saw blade guide in place will be sufficient that, with the saw blade guide removed, the remainder of the cut may readily be completed without the aid of a guide slot or surface.

Figure 14:
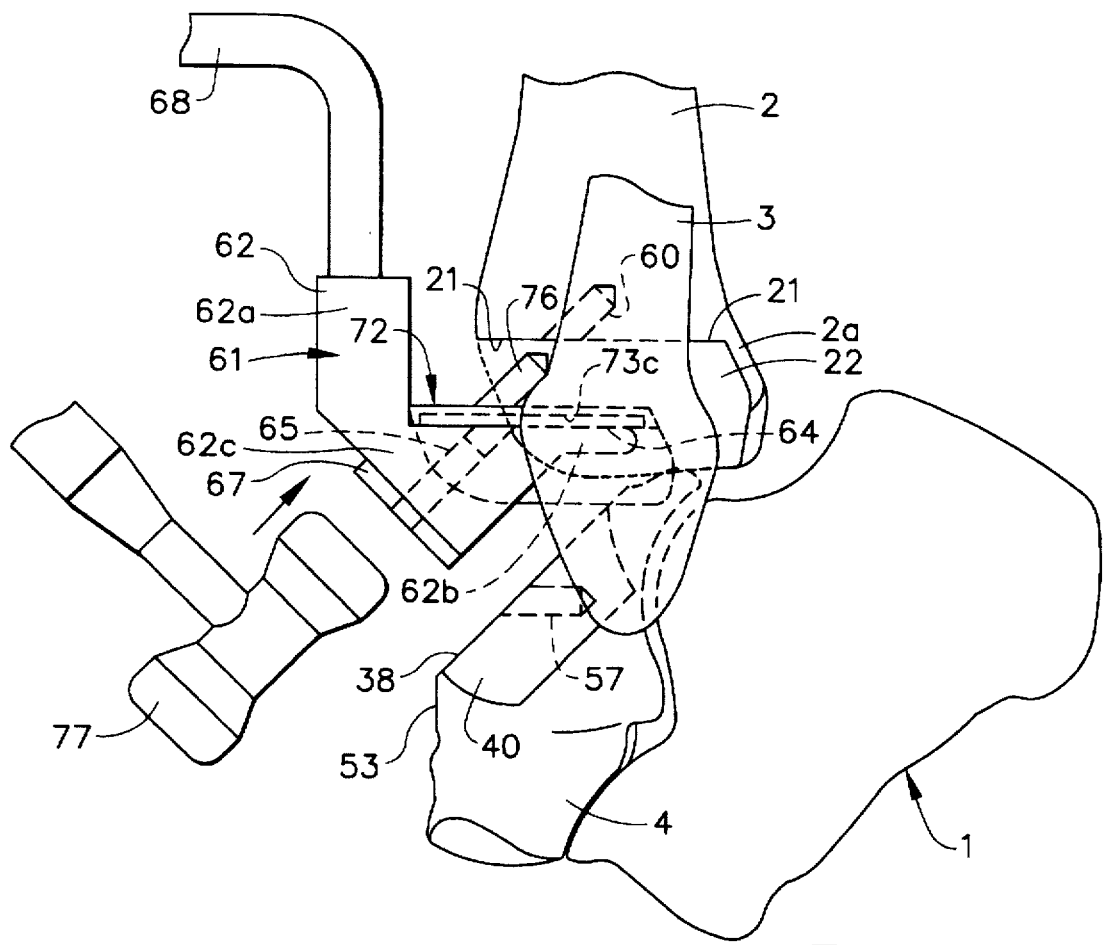
FIG. 14 is a fragmentary lateral elevational view, similar to FIG. 13, illustrating the use of the tibia drill guide to mount the tibial prosthesis component on the cut surfaces of the tibia.
Figure 15:
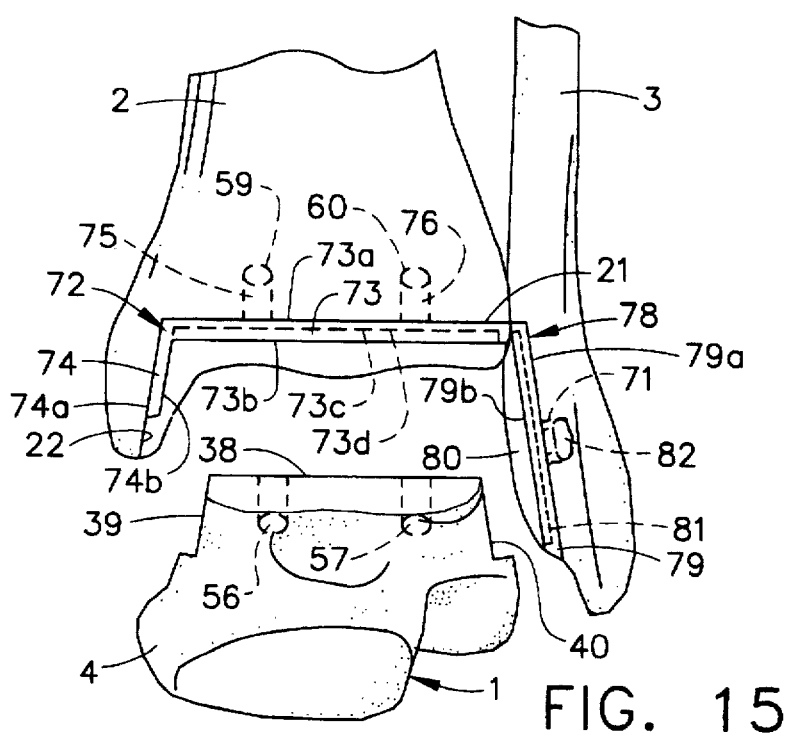
FIG. 15 is a fragmentary front elevational view illustrating the tibial and fibular prosthesis components in place.

Preparation of the tibia 2 for receipt of its prosthesis component is completed by providing the tibia with a pair of bores 59 and 60 in side-by-side relationship (see FIGS. 13, 14 and 15). The bores 59 and 60 are formed in the cut surface 21 of tibia 2 through the aid of a tool comprising a tibia drill guide, generally indicated at 61, having an L-shaped body 62 and a handle 68. The body 62 may be made of any appropriate material suitable for use in a surgical environment and capable of sterilization, such as stainless steel. The handle 68 is such as to enable the tibia drill guide 61 to be held in place during the drilling operation.

As viewed in FIG. 13, the vertical leg portion 62a of body 62 provides an abutment surface 63 for abutment against the anterior surface of tibia 2, as shown in FIG. 13. The horizontally oriented leg 62b of body 62 has a planar surface 64 adapted to abut the upper cut surface 21 of tibia 2. The leg portion 62b of body 62 has an enlarged portion 62c through which a pair of side-by-side drill bit guide bores extend, one of which is shown in FIG. 13 at 65. The axes of bore 65 and its companion bore (not shown) form an acute angle of 45° with the tibia drill guide surface 64. The portion 62c of tibia drill guide body 62 has a surface 66 which is perpendicular to the axes of bore 65 and its companion bore (not shown). The surface 66 may be provided with an additional layer 67, through which the bores extend, comprising a strike plate adapted to receive the blows of a mallet, as will be described hereinafter. During use of the tibia drill guide 61, the patient's foot 1 remains in the same plantar-flexed position shown in FIG. 10. The surface 64 of the tibia drill guide is located against the tibial surface 21, with the tibia drill guide surface 63 abutting the anterior portion of the tibia, as shown in FIG. 13. This is accomplished by means of a handle 68 affixed to the vertical leg portion 62a of tibia drill guide 61. The handle 68 can be used to maintain the tibia drill guide 61 in place throughout the drilling operation. Conventional surgical drill 55 and its bit 54 are used to form the bores 59 and 60 in the tibia. Once again, the collar 58 may be provided on drill bit 54 to determine the gauge or depth of bores 59 and 60.

As is suggested in FIG. 13 and shown in FIG. 14, the bores 59 and 60 have axes which form an angle of about 45° with respect to the tibial cut surface 21. Since the bores 59 and 60 are formed in the soft central part of the tibia, it would be possible to substitute for the tibia drill guide 61 a somewhat similarly shaped tool having a surface corresponding to surface 64 of the tibia drill guide and from which a pair of pointed spikes extend upwardly at an angle of about 45°. The spikes would be used to form the bores 59 and 60 by blows applied to the tool with a surgical mallet or the like. While such a tool and procedure could be used successfully, a more precise location of the bores 59 and 60 will be achieved with the tibia drill guide heretofore described. Furthermore, the tibia drill guide 61 can be used to serve an additional purpose, as will be described hereinafter. The bores 56 and 57 in the surface 38 of talus 4 could also be formed by means of a tool bearing a pair of appropriately located spikes and driven into the soft central part of the talus by a surgical mallet or the like. Again, a tool such as the chamfer cut and drill guide 41 is preferred.

The final bone preparation in the procedure of the present invention is that of the fibula. As is indicated in FIG. 12, the sharp edged bowl portion 69 of a cruette 70 is used to form a small blind bore 71 in the cut surface 23 of fibula 3. The purpose of blind bore 71 will be apparent hereinafter. With the formation of blind bore 71, the tibia 2, fibula 3 and talus 4 are all ready to receive their respective prosthesis components.

Reference is made to FIGS. 14 and 15, wherein the tibial prosthesis component is generally shown at 72. The tibial prosthesis component comprises a metallic member made of a metal alloy which is biocompatible and suitable for the purpose. Titanium alloys, for example, have long been used for various types of prosthesis components. Titanium alloys are biocompatible and have been shown to have good wear characteristics and to have certain elastic characteristics which contribute to their biocompatibility. The tibial prosthesis component 72, as viewed in FIGS. 14 and 15 has an upper portion 73 and a downwardly and outwardly depending medial portion 74. Both the outside and inside surfaces 74a and 74b of medial portion 74 are substantially planar. The same is true of the top and bottom surfaces 73a and 73b of the upper portion 73. As is shown in FIG. 14, the bottom surface 73b (See FIG. 15) of the top portion 73 has a depression 73c formed therein (see FIGS. 14 and 15). The interior surface 73d of depression 73c (See FIG. 15) is planar and parallel with the top surface 73a of upper portion 73. The purpose of depression 73c and its planar interior surface 73d will be apparent hereinafter. The upper surface 73a is adapted to abut the tibial cut surface 21. The outer surface 74a of medial portion 74 is adapted to abut tibial cut surface 22. The tibial prosthesis component 72 is completed by the provision on the top surface 73a of upper portion 73 of a pair of mounting pins 75 and 76. The mounting pins 75 and 76 constitute integral one-piece parts of the prosthesis component 72 and form an angle of about 45° with the top surface 73a of prosthesis 72.

To mount prosthesis component 72 in place, the prosthesis component may be laid upon the planar surface 64 of the body 62 of tibia drill guide 61. The anterior edge of prosthesis component 72 is abutted against body portion 62a of tibia drill guide 61. The tibia drill guide 61 is then shifted forwardly and upwardly so as to introduce the mounting pins 75 and 76 into the tibia bores 59 and 60, respectively. A surgical mallet 77 is then used to apply light blows to the strike plate 67 of the tibia drill guide 61 until the prosthesis component 72 is fully seated against tibial surfaces 21 and 22, as shown in FIG. 15. Depending upon the patient, the prosthesis component surfaces 73a and 74a may be adhered to tibial cut surfaces 21 and 22 by a surgically acceptable cement such as methyl methacrylate. Alternatively, the prosthesis surfaces 73a and 74a may have pores formed therein to accommodate bio-ingrowth.

As a next step, the fibular prosthesis component is mounted in place. The fibular prosthesis component is generally indicated at 78 in FIG. 15. The fibular prosthesis component comprises a metallic member 79 and a plastic insert 80. The metallic member 79 is made of a biocompatible metallic alloy such as a titanium alloy. The metallic member 79 has a somewhat heart-shaped peripheral configuration (generally matching the peripheral shape of the adjacent lower end of the fibula) with a planar lateral surface 79a and a planar medial surface 79b. A recess 81 is formed in medial surface 79b. The plastic insert 80 is affixed to the metallic portion 79 within recess 81 by adhesive means or the like. Plastic insert 80 may be made of any appropriate synthetic plastic material suitable for the purpose and suitable for a surgical environment. High density polyethylene is an excellent plastic material for this purpose, widely used in other surgical devices and characterized by excellent wear resistance and a low coefficient of friction. The medial surface of insert 80 approximates the original medial surface of the fibula 3. The metallic member of the fibular prosthesis component 78 has, on its lateral surface 79a, a stud 82 adapted to be received within blind bore 71. The stud 82 may be press fitted into blind bore 71 or cemented therein by means of a biocompatible adhesive such as the above-mentioned methyl methacrylate. The fibular prosthesis component 78 may be positioned and held in place until the adhesive material has set by an appropriate clamping tool.

Figure 16:
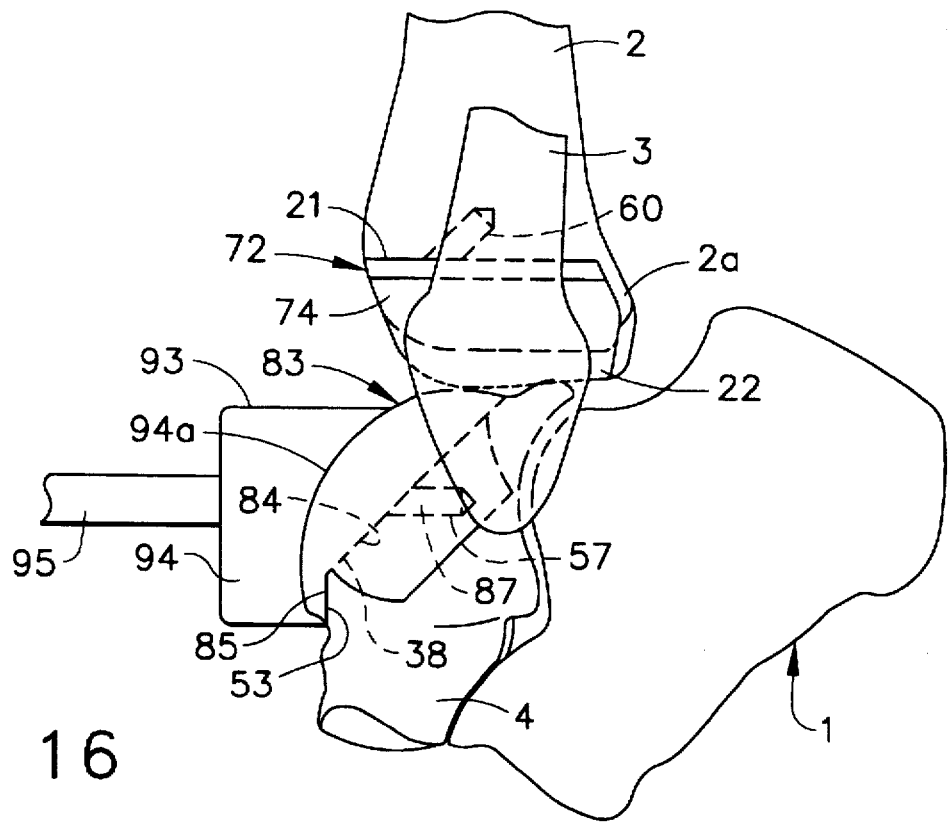
FIG. 16 is a fragmentary lateral elevational view, similar to FIG. 14 and illustrating the use of an impactor to mount the talar prosthesis component on the cut surfaces of the talus.
Figure 17:
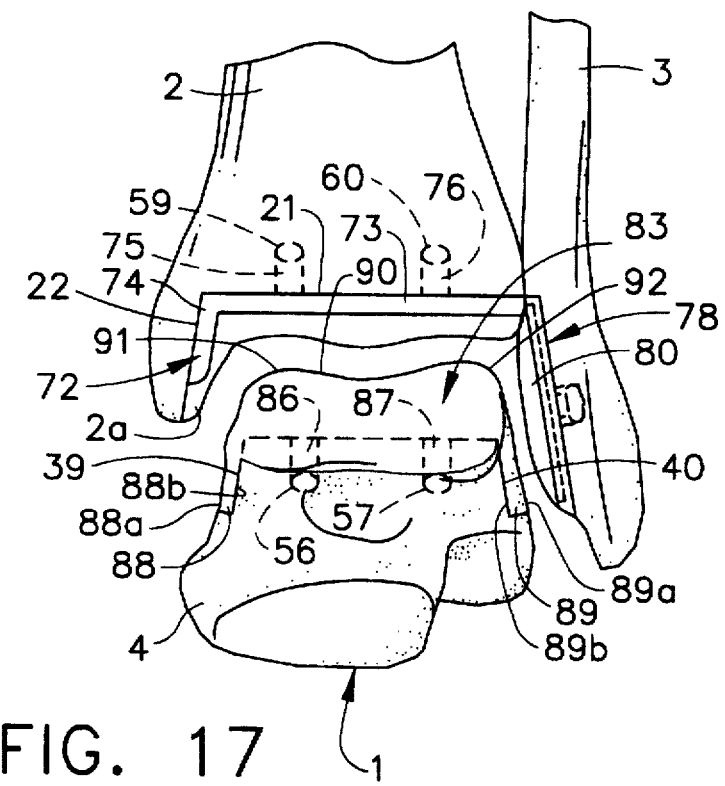
FIG. 17 is a fragmentary front elevational view of the tibia, fibula, and talus with the tibial, fibular and talar prosthesis components in place.

Reference is now made to FIGS. 16 and 17. The next step in the procedure of the present invention is the mounting of the talar prosthesis component on the talus, itself. The talar prosthesis component comprises a metallic member made of an alloy suitable for use in a surgical environment, such as a titanium alloy of the type described above. The talar prosthesis component is generally indicated at 83 in FIGS. 16 and 17. Talar prosthesis component 83 has a planar surface 84 adapted to abut talar cut surface 38. Prosthesis component 83 has a second planar surface 85 lying at an angle of 135° with respect to surface 84 and adapted to abut talar anterior chamfer cut surface 53. A pair of mounting pins 86 and 87 extend from prosthesis component surface 84 at an angle of 45° thereto. The mounting pins 86 and 87 are adapted to be received in the bores 56 and 57 formed in the talar cut surface 38.

The talar prosthesis component 83 has a medial portion 88 with an outside surface 88a and an inside surface 88b. The inside surface 88b is adapted to abut the talar medial cut surface 39. The prosthesis component 83 has a lateral portion 89 with an outside surface 89a and an inside surface 89b. The inside surface 89b is adapted to abut the talar cut surface 40. The outer surface 88a of medial portion 88 is adapted to cooperate with a floating bearing, to be described hereinafter. The outer surface 89a of lateral portion 89 is adapted to cooperate with insert 80 of fibular prosthesis component 78. The exterior surfaces 88a and 89a, together with the exterior surface 90 of the main body portion of the talar prosthesis component 83 are intended to approximate the original exterior surface of the corresponding portions of the talus. As is best seen in FIG. 17, the surface 90 comprises a medial arc 91 and a lateral arc 92. The arc 91 is of a lesser radius than the arc 92, but they are concentric (i.e. their respective radii extend from the same axis).

The talar prosthesis component may be affixed to talar surfaces 38, 39, 40 and 53 by adhesive means such as methyl methacrylate. Alternatively, depending upon the patient, the prosthesis component surfaces 84, 85, 88b and 89b may be provided with pores to accommodate bio-ingrowth. The prosthesis component 83 is applied to the talus 4 preferably by hand. Once it is at least partially located on the talus with its mounting pins 86 and 87 started in their respective bores 56 and 57, the talar prosthesis component 83 can be engaged by an appropriate tool in the form of an impactor 93 (see FIG. 16). Impactor 93 has a body portion 94 with a cavity 94a adapted to receive and engage the exterior surface of prosthesis component 83. The body 94 is provided with a handle 95. Blows may be applied to the impactor 93 by a surgical mallet of the type shown at 77 in FIG. 14, causing the mounting pins 86 and 87 to seat in talar bores 56 and 57, respectively and prosthesis component surfaces 84 and 85 to abut talar cut surfaces 38 and 53, respectively. The body 94 of impactor 93 is preferably made of high density polyethylene or a similar plastic material suitable for use in a surgical environment. This assures that the exterior surface 90 of the talar prosthesis component 83 will not be scored or scratched by impactor 93.

Figure 18:
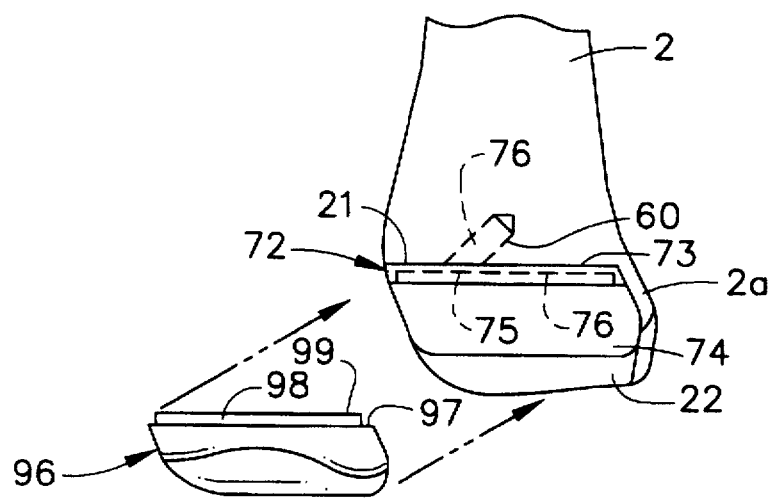
FIG. 18 is a fragmentary lateral elevational view illustrating the tibial prosthesis component in place and the floating bearing of the present invention ready for mounting.
Figure 19:
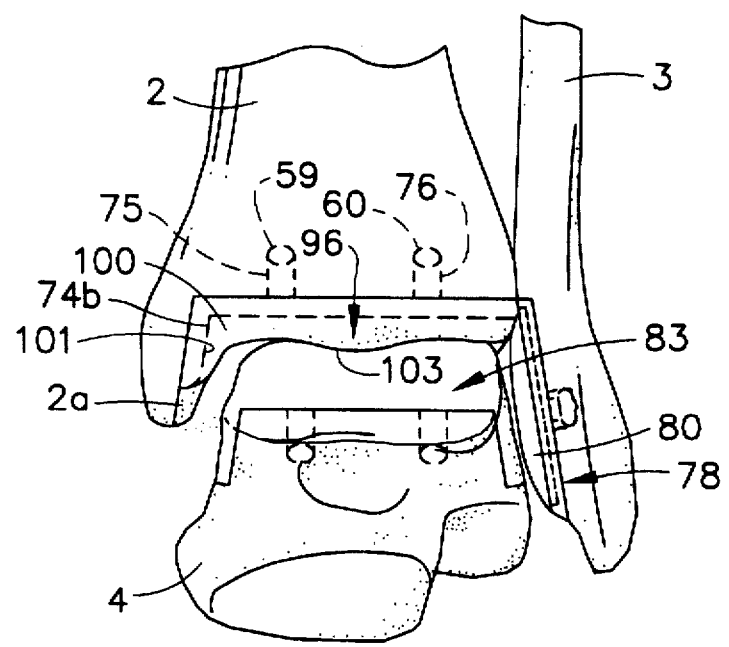
FIG. 19 is a fragmentary front elevational view, similar to FIG. 17, showing the floating bearing in place, completing the total ankle prosthesis of the present invention.

The ankle replacement of the present invention is completed by the provision of a floating bearing (see FIGS. 18 and 19). The floating bearing is generally indicated at 96 and is made of a synthetic plastic material such as the aforementioned high density polyethylene because it is widely accepted for surgical uses, has a low coefficient of friction and has excellent wear resistance. The floating bearing 96 has a planar top surface 97 with a raised central portion 98 terminating in a planar upper surface 99. The raised central portion 98 is adapted to be received in the depression 73c of the tibial prosthesis component 72. It will be noted from FIG. 18 that the floating bearing raised central portion 98 has an anterior-posterior dimension less than the anterior-posterior dimension of the tibial prosthesis component depression 73c so that the floating bearing 96 is shiftable therein in fore and aft (i.e. anterior-posterior) directions. Similarly, the raised central portion 98 of floating bearing 96 preferably has a medial-lateral dimension slightly less than that of tibial prosthesis component depression 73c, so that there is some side motion or medial-lateral motion between floating bearing 96 and tibial prosthesis component 72.

The floating bearing 96 has a medial portion 100 which has an outside surface 101 adapted to abut and slide along surface 74b of the tibial prosthesis component 72. The inside surface 103 of the floating bearing 96 is configured to cooperate with the outside surface 90 of the talar prosthesis component 83.

The floating bearing may be properly located and seated within the ankle joint, between the tibial prosthesis component 72 and the talar prosthesis component 83, by hand. The floating bearing is inserted into the ankle joint with the foot in plantarflexed position. FIG. 19 illustrates the completed ankle joint with all of the prosthesis components and floating bearing in place. The talar prosthesis component 83 and the floating bearing have a total contact relationship.

If the completed ankle joint is too lax, a floating bearing of greater thickness may be chosen. Similarly, if the completed ankle joint is too tight, a floating bearing of lesser thickness can be used. Selection of the floating bearing of proper thickness permits adjustment of the overall height of the prosthesis and would permit revision and use of trial components.

It will be understood by one skilled in the art that the tibial prosthesis component 72, the fibular prosthesis component 78, the talar prosthesis component 83 and the floating bearing component 96 will all have to be made in left and right mirror-image embodiments and will all have to be made in a number of sizes to accommodate patients of different sizes. The number of sizes does not constitute a limitation of the present invention. It is believed, for example, that a wide range total ankle replacements could be accommodated by providing each of these elements in three sizes. The floating bearing component 96 should also be made in various thicknesses for reasons given above.

It will further be understood that the various tools such as the tibia/fibula saw guide 9, the talus saw guide 24, the drill and chamfer guide 41, the tibia drill guide 61, and the impactor 93 may also have to be made in left and right embodiments and in various sizes to accommodate the corresponding prosthesis components and floating bearing sizes. Each of the aforementioned tools has a handle which may be permanently affixed thereto. In the alternative, the handle may be affixed to their respective tool bodies by any appropriate means including snap-on or quick-release means so that each handle can serve as the handle for each size of its respective tool right and left embodiments.

Finally, it will be appreciated by one skilled in the art that the various interacting surfaces of the prosthesis components, including the floating bearing component are intended to approximate the shape of the bone surfaces they replace. The interacting prosthesis components are not intended to be exact replicas of the surfaces they replace. The prosthesis components are provided with similar surfaces engineered to transfer loads within the constraints of and characteristics of the prosthesis components themselves. The prosthesis components (including the floating bearing) of the present invention accommodate the changing centers of rotation of the talus with respect to the tibia. They also permit the full range of motion of the fibula including sliding motion fore and aft, piston-like motion up and down, and rotation.

Modifications may be made in the invention without departing from the spirit of it.

What is claimed:

1. A total ankle replacement adapted to involve the patient's tibia, talus and fibula comprising a total ankle prosthesis including a tibial component for mounting on at least a part of a prepared tibial surface, a talar component for mounting on at least a part of a prepared talar surface, a fibular component for mounting on at least a part of a prepared fibular surface and a floating bearing component, said floating bearing component being located between said tibial and talar components, said floating bearing component being configured to effect limited predetermined fore and aft, medial-lateral and rotational movement with respect to said tibial component, said floating bearing component making full contact with said talar component, said fibular component cooperating with said talar component to substantially retain the normal fibular movements including sliding motion fore and aft, piston-like motion up and down and rotation.

2. The total ankle replacement claimed in claim 1 wherein said tibial prepared surface comprises a cut surface at the distal end of the tibia having a planar main portion and a planar downwardly and outwardly extending medial portion.

3. The total ankle replacement claimed in claim 2 wherein said tibial prosthesis component comprises a metallic component having a planar substantially horizontal top surface and a downwardly and outwardly extending medial surface, said top and medial surfaces adapted to be affixed to said tibial cut surface main portion and said downwardly and outwardly extending cut surface medial portion, respectively, said tibial prosthesis component having a substantially planar downwardly facing surface with a shallow recess formed therein, said recess having a planar downwardly facing inner surface.

4. The total ankle replacement claimed in claim 3 wherein said floating bearing component comprises a plastic member, said floating bearing component having a planar top surface with a raised central portion formed thereon, said raised central portion having a planar top surface, said floating bearing component raised central portion being receivable with clearance in said recess in said tibial component with said planar top surface of said raised central portion abutting said planar inner surface of said recess, the relative dimensions of said recess and said raised central portion determining the extent of said fore and aft, medial—lateral and rotational movements of said floating bearing component with respect to said tibial component.

5. The total ankle replacement claimed in claim 2 wherein said prepared fibular surface comprises a planar cut surface extending downwardly and outwardly on the medial face of the fibula near the distal end portion thereof.

6. The total ankle replacement claimed in claim 2 wherein said tibial prosthesis component has two integral locating and mounting pins thereon which, when said tibial prosthesis component is properly mounted on said tibial prepared surface, are receivable in two bores formed in said planar main portion of said prepared surface of said tibia, said bores being parallel and being directed downwardly and inwardly of said planar main surface at an angle of about 45°.

7. The total ankle replacement claimed in claim 1 wherein said prepared fibular surface comprises a planar cut surface extending downwardly and outwardly on the medial face of the fibula near the distal end portion thereof.

8. The total ankle replacement claimed in claim 7 wherein said fibular component comprises a metallic component having a planar lateral surface adapted to be affixed to said fibular prepared surface, said fibular prosthesis component having a medial surface with a shallow recess formed therein, a plastic insert adapted to be affixed in said recess and having a medial surface approximating the natural surface of said fibula replaced by said fibular component.

9. The total ankle replacement claimed in claim 8 wherein said fibular prosthesis component has an integral stud thereon receivable in a depression in said fibular prepared surface.

10. The total ankle replacement claimed in claim 1 wherein said talus has an upper dome-shaped portion, said talar prepared surface comprising a cut surface on said dome having a planar main portion terminating in downwardly and outwardly directed medial and lateral portions and a downwardly and outwardly directed forward chamfer portion.

11. The total ankle replacement claimed in claim 10 wherein said talar prosthesis component comprises a metallic component having surfaces corresponding to and adapted to be affixed respectively to said main portion, said medial and lateral portions, and said forward portion of said prepared surface of said talus, said talar prosthesis component having an upper surface approximating the natural talar surface replaced by said talar prosthesis component including medial and lateral arcs.

12. The total ankle replacement claimed in claim 11 wherein said floating bearing component comprises a plastic member, said floating bearing component having a planar top surface with a raised central portion formed thereon, said raised central portion having a planar top surface, said floating bearing component raised central portion being receivable with clearance in a recess in said tibial component with said planar top surface of said raised central portion abutting a planar inner surface of said recess, the relative dimensions of said recess and said raised central portion determining the extent of said fore and aft, medial—lateral and rotational movements of said floating bearing component with respect to said tibial component, said floating bearing component having a lower surface configured for a total contact relationship with said upper surface of said talar component.

13. The total ankle replacement claimed in claim 10 wherein said talar component has two integral locating and attachment pins which, when properly mounted on said talar prepared surface, are receivable in two bores formed in said planar main portion of sad prepared surface of said talus, said bores being parallel and being directed downwardly and inwardly of said planar main surface at an angle of about 45°.

14. The total ankle replacement claimed in claim 1 wherein said tibial prepared surface comprises a cut surface at the distal end of the tibia having a planar main portion and a planar downwardly and outwardly extending medial portion, said prepared fibular surface comprising a planar cut surface extending downwardly and outwardly on the medial face of the fibula near the distal end portion thereof, said talas having an upper dome-shaped portion, said talar prepared surface comprising a cut surface on said dome having a planar main portion terminating in downwardly and outwardly directed medial and lateral portions and a downwardly directed front portion.

15. A total ankle prosthesis comprising a tibial component, a talar component, a fibular component and a floating bearing component, said tibial, talar and fibular components being mountable on prepared tibial, talar and fibular surfaces respectively, said floating bearing being locatable between said tibial and talar components, said floating bearing being configured to effect limited predetermined fore and aft, rotational and medial and lateral movements with respect to said tibial component and capable of full contact with said talar component, said fibular component being configured to cooperate with said talar component to substantially retain normal fibular movements including sliding motion fore and aft, piston-like motion up and down and rotation.

16. The total ankle prosthesis claimed in claim 15 wherein said tibial prosthesis component comprises a metallic component having a planar substantially horizontal top surface and a downwardly and outwardly extending medial surface corresponding to said tibial prepared surfaces, said tibial prosthesis component having a substantially planar downwardly facing surface with a shallow recess formed therein, said recess having a planar downwardly facing inner surface.

17. The total ankle prosthesis claimed in claim 15 wherein said fibular component comprises a metallic component having a planar lateral surface with an integral stud thereon corresponding to said fibular prepared surface, said fibular component having a medial surface with a shallow recess formed therein, a plastic insert being affixed in said recess and having a medial surface approximating the natural fibular surface to be replaced thereby.

18. The total ankle replacement claimed in claim 15 wherein said talar prosthesis component comprises a metallic component having surfaces corresponding to and adapted to be affixed to a main portion of said prepared surface of said talus, said talar prosthesis component having an upper surface approximating the natural talar surface replaced by said talar prosthesis component including medial and lateral arcs.

19. The total ankle replacement claimed in claim 15 wherein said floating bearing comprises a plastic number, said floating bearing having a planar top surface with a raised central portion formed thereon, said raised central portion having a planar top surface, said floating bearing raised central portion abutting and cooperating with said tibial prosthesis component to determine the extent of said fore and aft, said rotational and said medial and lateral movements of said floating bearing with respect to said tibial prosthesis component, said floating bearing having a lower surface configured for a total contact relationship with an upper surface of said talar prosthesis component.

20. A total ankle replacement adapted to involve the patient's tibia, talus and fibula comprising:

(a) a tibial component for mounting on at least a part of a prepared tibial surface, said tibial component comprising an upper portion and a downwardly and outwardly depending medial portion, said medial portion comprising substantially planar outside and inside surfaces, said upper portion comprising substantially planar top and bottom surfaces, said bottom surface of said top portion further comprising a depression, said depression comprising an interior surface, said interior surface of said depression being substantially planar and parallel with said top surface of said upper portion;

(b) a talar component for mounting on at least a part of a prepared talar surface, said talar component comprising a medial portion having a first outside surface, said talar component further comprising a lateral portion having a second outside surface, said talar component further comprising a main body having an exterior surface, said main body exterior surface comprising a medial arc and a lateral arc, said medial arc and said lateral arc being concentric, said medial arc having a lesser radius than said lateral arc so that said first and second outside surfaces and said exterior surface together substantially approximate the surface of a human talus;

(c) a fibular component for mounting on at least a part of a prepared fibular surface said fibular component comprising a fibular contacting component having a substantially planar lateral surface, said fibular contacting component having a peripheral configuration generally approximating the peripheral shape of the adjacent lower end of the fibula, said fibular component rather comprising an insert adapted to be affixed in a recess of said fibular contacting component, said insert having a medial component that substantially approximates the natural surface of a human fibula; and (d) a floating bearing component, said floating bearing component being located between said tibial and talar components, said floating bearing component being configured to limited predetermined fore and aft, medial-lateral and rotational movement with respect to said tibial component, said floating bearing component making full contact with said talar component, said fibular component cooperating with said talar component to substantially retain the normal fibular movements including sliding motion fore and aft, piston-like motion up and down, and rotation.

\* \* \* \* \*

UNITED STATES PATENT AND TRADEMARK OFFICE
CERTIFICATE OF CORRECTION

PATENT NO.    :   5,766,259
DATED         :   June 16, 1998
INVENTOR(S)   :   Giacomo J. Sammarco It is certified that error appears in the above-indentified patent and that said Letters Patent is hereby corrected as shown below:

In column 12, line 28, delete "sad" and insert -- said -- therefor.

In column 14, line 21, delete "rather" and insert -- further -- therefor.

In column 14, line 28, after "to" insert -- effect --.

Signed and Sealed this

Eighth Day of September, 1998

Attest:

BRUCE LEHMAN

Attesting Officer

Commissioner of Patents and Trademarks